(12) United States Patent
Boulais

(10) Patent No.: US 7,811,277 B2
(45) Date of Patent: Oct. 12, 2010

(54) STEERABLE DEVICE AND SYSTEM

(75) Inventor: Dennis R. Boulais, Danielson, CT (US)

(73) Assignee: Boston Scientific Scimed, Inc., Natick, MA (US)

( * ) Notice: Subject to any disclaimer, the term of this patent is extended or adjusted under 35 U.S.C. 154(b) by 1060 days.

(21) Appl. No.: 10/955,930

(22) Filed: Sep. 30, 2004

(65) Prior Publication Data

US 2006/0074383 A1    Apr. 6, 2006

(51) Int. Cl.
*A61M 25/00* (2006.01)
(52) U.S. Cl. .................................................. 604/528
(58) Field of Classification Search .............. 604/95.04, 604/170.03, 528, 534–535
See application file for complete search history.

(56) References Cited

U.S. PATENT DOCUMENTS

| | | | |
|---|---|---|---|
| 5,179,934 A | | 1/1993 | Nagayoshi et al. |
| 5,381,782 A | | 1/1995 | DeLaRama et al. |
| 5,496,260 A | | 3/1996 | Krauter et al. |
| 5,846,183 A | | 12/1998 | Chilcoat |
| 5,944,690 A | * | 8/1999 | Falwell et al. .......... 604/170.03 |
| 6,033,378 A | * | 3/2000 | Lundquist et al. ......... 604/95.01 |
| 6,610,007 B2 | * | 8/2003 | Belson et al. ............... 600/146 |
| 6,648,875 B2 | * | 11/2003 | Simpson et al. ............ 604/528 |
| 6,663,588 B2 | * | 12/2003 | DuBois et al. ........... 604/95.04 |
| 2003/0181855 A1 | * | 9/2003 | Simpson et al. ......... 604/95.04 |

FOREIGN PATENT DOCUMENTS

EP    1 177 809 A1    2/2002

* cited by examiner

*Primary Examiner*—Kevin C Sirmons
*Assistant Examiner*—Bradley J Osinski
(74) *Attorney, Agent, or Firm*—Finnegan, Henderson, Farabow, Garrett & Dunner, LLP

(57) ABSTRACT

A system includes a steerable device, such as a sheath or shaft, having proximal and distal ends. The steerable device includes an elongated body having a proximal section, a steering section, and a distal tip. Control wires are routed through the body and connected at or near the distal end of the steerable device. The system further includes a control unit to which the proximal end of the steerable device is functionally connected. In one embodiment, the control unit includes an actuator connected to one control wire and a biasing force generating device connected to a second control wire. The steering section is controllably manipulated by the control unit to facilitate steering of the distal tip of the steerable device as the steerable device is advanced through tortuous passageways of a patient's body.

23 Claims, 9 Drawing Sheets

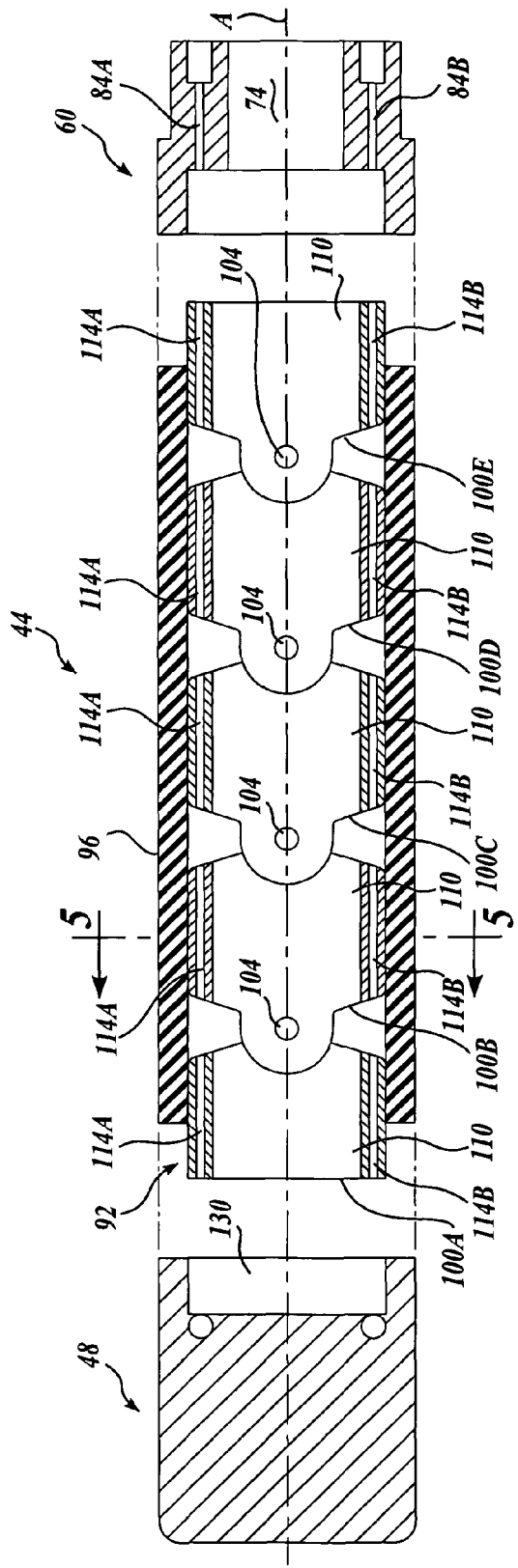

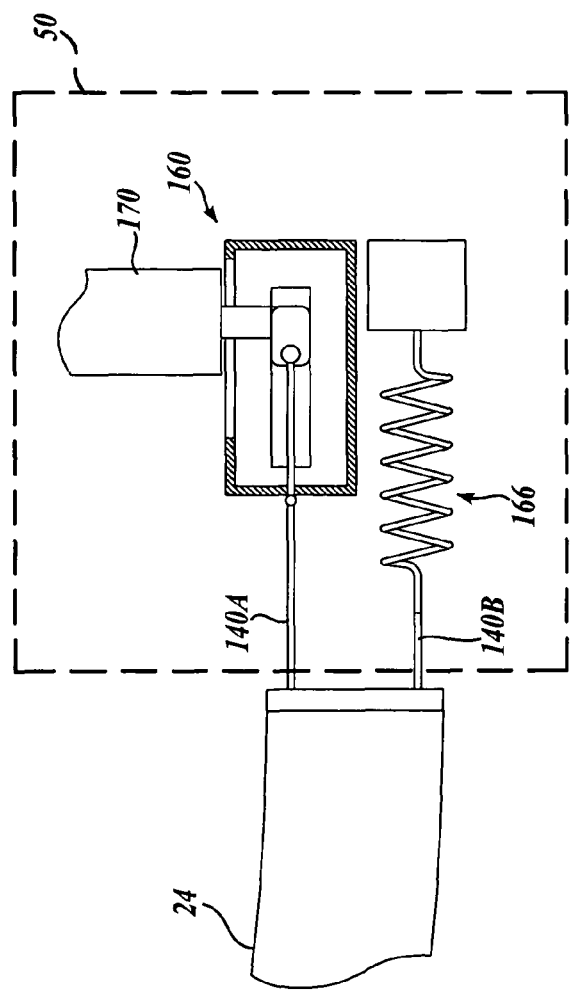
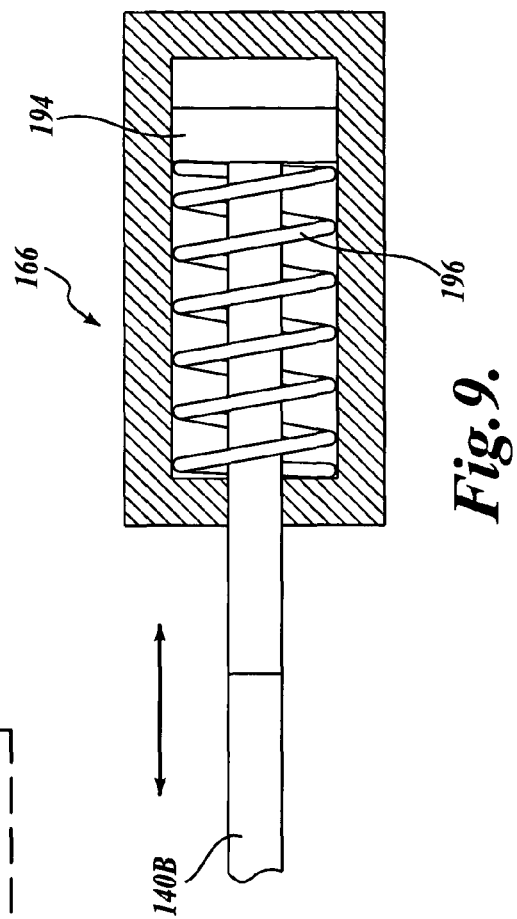
Fig. 8.
Fig. 9.

STEERABLE DEVICE AND SYSTEM

FIELD OF THE INVENTION

In general, the present invention is directed to systems suitable for use in medical procedures, and in particular, to medical systems that include a steerable device that is controlled by a control unit at the proximal end thereof.

BACKGROUND OF THE INVENTION

Endoscopes and imaging catheters are widely used in many medical procedures for viewing areas of bodily organs, cavities, passageways, etc. Generally, such imaging devices include an elongate sheath or similar structure wherein optical fibers are arranged both for transmitting illumination light to the distal end of the sheath to illuminate a viewing field, and for carrying an optical image back to a viewing port or camera. One or more lenses may be positioned on the distal end of the imaging device to focus the optical image received by, or the illumination cast by the instrument.

In many applications, it is desirable that the distal portion of the imaging device be "steerable", bendable or maneuverable from the proximal end of the device to facilitate guidance of the device through tortuous or furcated anatomical passageways. Additionally, the ability to bend the device at or near its distal end may enable the operator to visually scan an expanded viewing area by bending or otherwise manipulating the distal end of the device Second, the ability to maneuver the tip makes it easier to guide the tip of the device properly through the often highly branched and convoluted passageways near organs such as the coronary arteries of the heart or the branched ducts of the biliary tree.

In order to effect and control the deflection of the distal tip of an imaging device, many designs have been introduced that incorporate either two opposed control wires to control bending in one plane or four wires evenly spaced to control bending in two perpendicular planes. These control wires run the length of the device and terminate at the distal end of the steerable region or at the distal tip. The proximal end of each control wire is functionally connected to a separate drum or spool rotated by a dedicated electrical or fluid motor for linearly advancing and retracting the control wire in relation to the device. In operation, when one of the control wires is pulled proximally by rotation of the drum or spool, the distal tip of the device bends at the steerable region toward the retracted wire.

SUMMARY OF THE INVENTION

Embodiments of the present invention are directed to systems that include steerable devices that maintain full steerability while reducing the total number of motors or actuators needed to bend the distal tip of the device with 2-way articulation in one plane or 4-way articulation in more than one plane. In accordance with one embodiment of the present invention, a system is provided that includes a steerable device, such as a sheath or shaft, and a control unit. The steerable device includes first and second control wires connected at or near the distal end that extend from the proximal end thereof. The control unit includes an actuator connected to the proximal end of the first control wire and a biasing force generator connected to the proximal end of the second control wire.

In accordance with aspects of the present invention, a system is provided. The system includes an elongate flexible device having proximal and distal ends and a longitudinal axis. The device includes a steerable section and a distal tip disposed at the distal end. The device is bendable at the steerable section for deflecting the distal tip in at least a first and a second direction. The system further includes at least first and second control wires having proximal and distal ends. The first and second control wires are routed through the flexible device. The distal ends of the first and second control wires are coupled at or near the distal end of the flexible device, whereby movement of the first control wire proximally deflects the distal tip in the first direction and movement of the second control wire proximally deflects the distal tip in the second direction. The distal tip is biased in the first direction by force applied to the first control wire.

In accordance with another aspect of the present invention, a system is provided. The system includes a device having proximal and distal ends and being deflectable between a series of positions, and first and second control wires having proximal and distal ends. The movement of the control wires causes the distal end to be deflected between the series of positions. The system further includes a control unit functionally connected to the proximal end of the device. The control unit including at least one actuator connected to the proximal end of the first or second wire and at least one force generating device connected to the proximal end of the other of the first or second control wire. The force generating device applies a first force on the first or second wire when the distal end is deflected to a first position, and applies a second force different than the first force on the first or second control wire when the distal tip is bent to a second position.

In accordance with another aspect of the present invention, a system is provided. The system includes an elongated device having a proximal end, a bendable distal section, and a distal end. The system also includes first and second control wires routed through the device. The distal ends of control wires are connected at or near the distal end of the device. The system further includes means for applying a biasing force on the first or second control wire in the proximal direction thereof.

In accordance with yet another aspect of the present invention, a system is provided. The system includes a steerable device including an elongate flexible body having proximal and distal ends, and a bendable section positioned near the distal end. The bendable section is manipulatable in at least one plane. the steerable device further includes at least first and second control wires having proximal and distal ends. The first and second wires are routed through the body. The distal ends of the first and second wires are coupled at or near the distal end of the body. The system further includes a control unit functionally connected to the proximal end of the device body. The control unit includes an actuator connected to the proximal end of the first control wire and a variable force generating device connected to the proximal end of the second control wire. The variable force generating device is capable of urging the second control wire in the proximal direction.

In accordance with yet another aspect of the present invention, an endoscopic system is provided. The system includes a shaft defining a centralized lumen and having proximal and distal ends, a bendable section at or near the distal end of the shaft for selectively orienting the distal end of the shaft, at least first and second control wires passed through the shaft and connected at or near the distal end of the shaft, and a control unit that controls the orientation of the distal end. The control unit includes an actuator that is connected to the proximal end of the first control wire and a biasing force generator that is connected to the proximal end of the second control wire.

In accordance with still another aspect of the present invention, a control device for use with a steerable medical device is provided. The control device includes at least one pair of control wires for deflecting a distal end of the medical device, a housing configured for receiving the pair of control wires, a drive member carried by the housing for pulling one control wire of the pair of control wires, and a biasing force generator carried by the housing. The biasing force generator is connected to other control wire of the pair of control wires. The control device further includes an actuator operably coupled to the drive member for effecting movement of the drive member.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 4 is a cross sectional view of the steerable section of the endoscope shown in FIG. 2;

FIG. 5 is a cross sectional view of the steerable section taken along lines 5-5 in FIG. 4;

FIG. 6 is a partial cross sectional view of an alternative embodiment of the proximal section of the endoscope shown in FIG. 2;

FIG. 8 is a partial view of an alternative embodiment of a control unit including a manually controlled actuator formed in accordance with one embodiment of the present invention;

FIG. 9 illustrates an alternative embodiment of a biasing force generating device suitable for use in the control unit.

DETAILED DESCRIPTION OF THE PREFERRED EMBODIMENT

The present invention will now be described with reference to the drawings where like numerals correspond to like elements. Embodiments of the present invention are directed to systems having steerable devices of the type broadly applicable to numerous medical applications in which it is desirable to insert the device into a body lumen or passageway. Embodiments of the steerable devices may include such features as illumination and visualization capabilities, for endoscopically viewing anatomical structures within the body when insertable therein. As such, embodiments of the present invention can be used for a variety of different diagnostic and interventional procedures, including colonoscopy, upper endoscopy, bronchoscopy, thoracoscopy, laparoscopy and video endoscopy, etc., and are particularly well suited for negotiating tortuous passageways of the human body. Although exemplary embodiments of the present invention will be described hereinafter as including endoscopes or endoscopic imaging devices, it will be appreciated that aspects of the present invention have wide application, and may utilize other medical devices, such as steerable imaging and non-imaging catheters (e.g., angioplasty catheters) or other flexible steering devices. Accordingly, the following descriptions and illustrations herein should be considered illustrative in nature, and thus, not limiting the scope of the present invention, as claimed.

Figure 1:
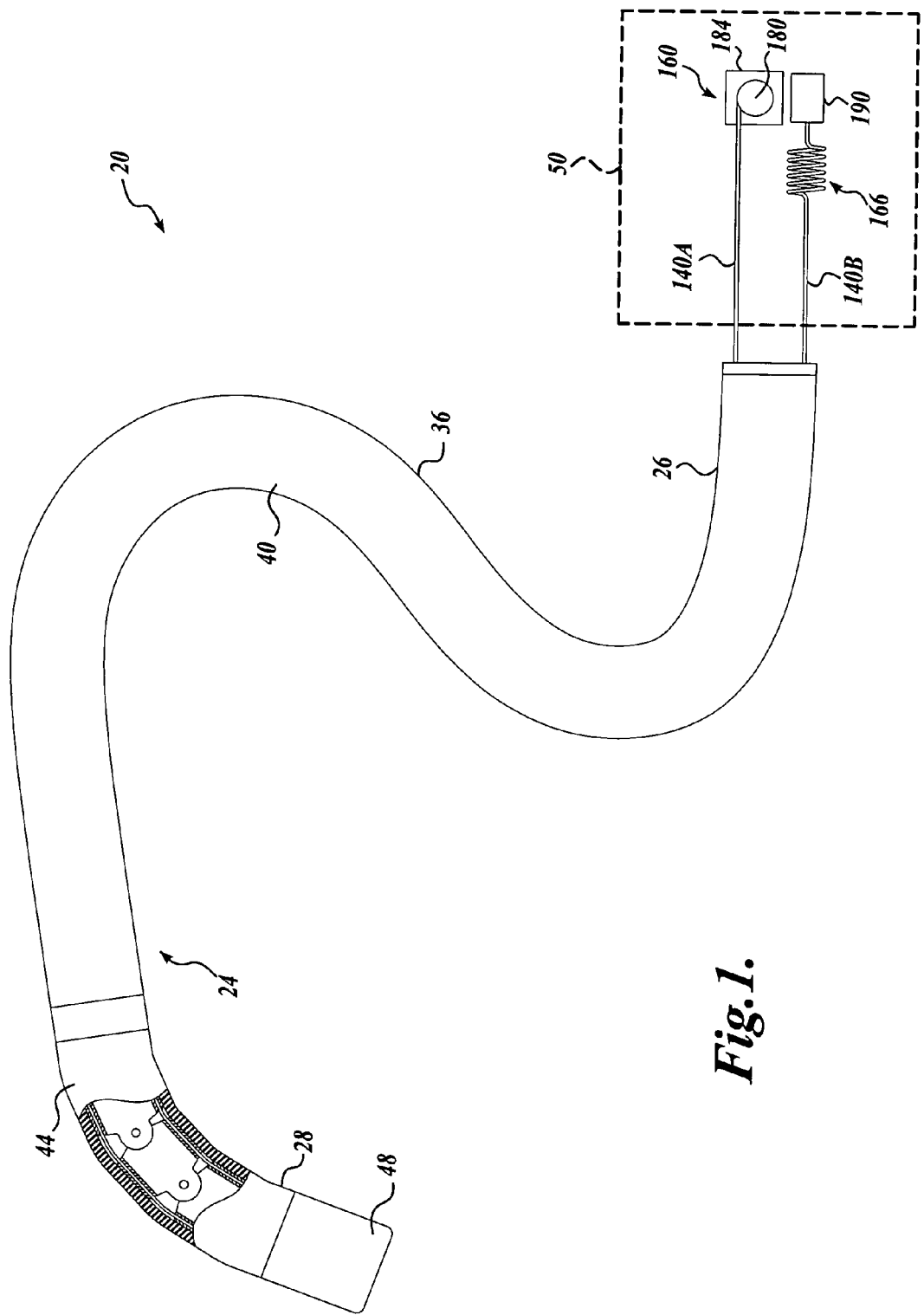
FIG. 1 illustrates one exemplary embodiment of a system formed in accordance with aspects of the present invention.

FIG. 1 illustrates one exemplary embodiment of a system 20 constructed in accordance with aspects of the present invention. The system 20 includes a steerable device 24 having a proximal end 26 and a distal end 28. The steerable device 24 includes an elongated shaft-like body 36 comprising a proximal section 40, a steering section 44, and a distal tip 48 disposed at the distal end 28 of the sheath 24. The system 20 further includes a control unit 50 to which the proximal end 26 of the steerable device 24 is functionally connected. As will be described in more detail below, the orientation of the steering section 44 is manipulated by the control unit 50 to facilitate steering of the distal tip 48 of the device 24 as the device 24 is advanced through tortuous passageways of the patient's body.

Figure 2:
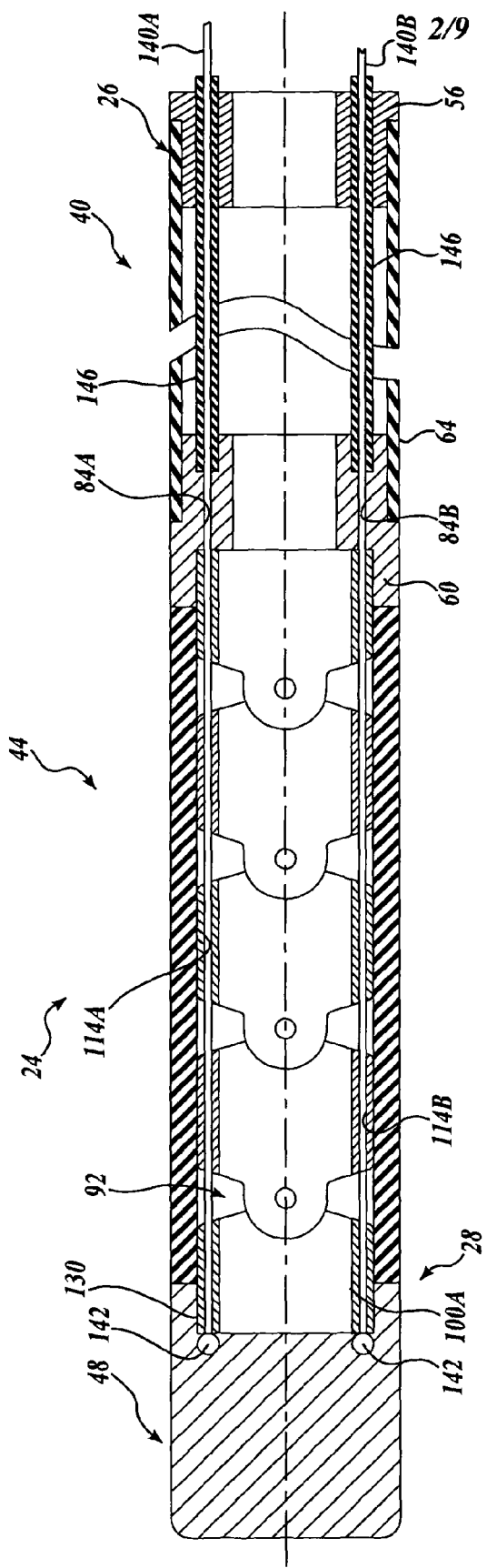
FIG. 2 is a cross sectional view of one embodiment of a steerable device, in particular, an endoscope in accordance with one embodiment of the present invention.

One suitable embodiment of the steerable device 24 will now be described in greater detail. As described above, the steerable device 24 includes a proximal section 40, a steering section 44, and a distal tip 48. As best shown in FIGS. 1 and 2, the proximal section 40 of the device body 36 begins at the proximal end 26 of the device 24 and extends along a majority of the device body's total length. The proximal section 40 may be of any suitable construction and made of any suitable material.

In one embodiment, the proximal section 40 includes a proximal cap 56 and a distal cap 60 interconnected by a flexible tubular sheath 64, as best shown in FIG. 2. The sheath 64 may be constructed of any suitable material that allows the device body 36 to navigate the tortuous paths of the patient's body but does not axially deform or compress, such as polyurethane, polypropylene, nylon, ABS or other biocompatible plastics. If desired, the sheath 64 may include a braid to increase its crush strength and/or its torsional rigidity.

Figure 3:
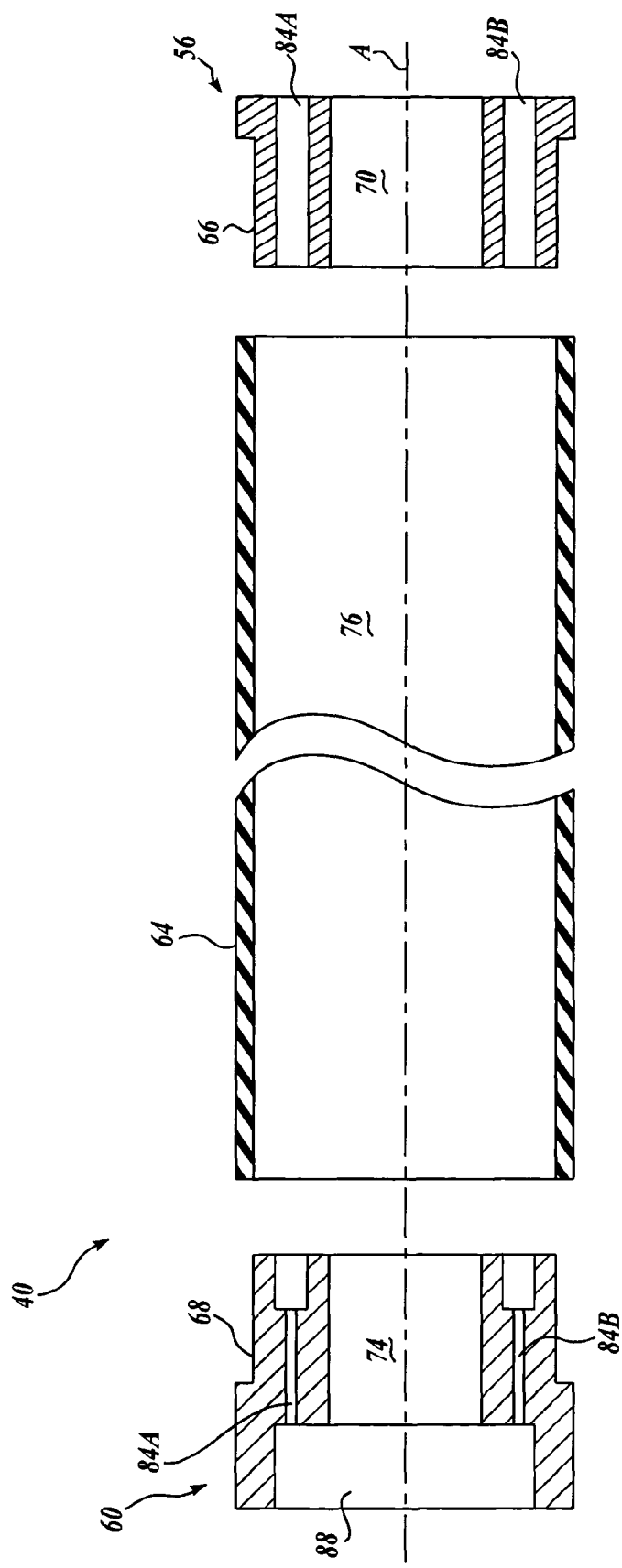
FIG. 3 is an exploded cross-sectional view of one embodiment of a flexible sheath section of the endoscope of FIG. 2.

In the embodiment shown in FIG. 3, the proximal and distal caps 56 and 60 are tubular members of circular cross-section constructed of any suitable biocompatible material, such as stainless steel or polyurethane, polypropylene, nylon, ABS or other biocompatible plastics. The proximal cap 56 is configured at its distal end with a reduced diameter portion 66. Similarly, the distal cap 60 is configured at its proximal end with a reduced diameter portion 68. Both reduced diameter portions 66 and 68 are sized and configured for insertion into the open ends of the tubular sheath 64 for connection therewith. The proximal and distal caps 56 and 60 define centralized passageways 70 and 74, respectively, concentrically arranged with the central lumen 76 defined by the tubular sleeve 64 for forming a contiguous central passageway through the proximal section 40 when assembled. As will be described in more detail below, the contiguous central passageway may allow for optics, working devices, fluid channels, or the like, to be routed to the distal tip of the device.

In one embodiment, the caps 56 and 60 are sized and configured such that when the reduced diameter portions 66 and 68 of the caps 56 and 60, respectively, are inserted into the ends of the tubular sheath 64 during assembly, the caps 56 and 60 are retained thereto by a friction fit. Alternatively, the ends of the sheath 64 may be coupled to the caps 56 and 60 by heat bonding, adhesive bonding, fasteners, or other techniques known in the art. In one embodiment, the components may be dimensioned such that when the reduced diameter portions 66 and 68 of the caps 56 and 60 are inserted into the ends of the tubular sheath 64, and abutted against the shoulders formed thereby, the outer surface of the sleeve 64 is flush with the remaining portion of the caps 56 and 60, thereby forming a section of the device 24 having a substantially constant diameter, as best shown in FIG. 2.

Returning now to FIG. 3, the proximal and distal caps 56 and 60 further define in their walls axially extending guide lumens 84 disposed radially offset from the longitudinal axis A of the device for accommodating smooth passage of control wires, as will be described in more detail below. In one embodiment, the caps 56 and 60 define first and second guide lumens 84A and 84B disposed 180 degrees from one another, the purpose of which will be described in more detail below. The distal cap 60 is further provided with a joint section 88 in the form of a recessed slot. The joint section 88 is sized and configured for connecting the distal end of the proximal section 40 to the proximal end of the steering section, as will be described in detail below.

While the proximal section 40 has been illustrated and described has an assembly of end caps interconnected by a tubular sheath, it will be appreciated that the proximal section may have other suitable constructions. For example, the proximal section 40 may be an integrally formed tube section 140 defining a central passageway 176 and a plurality of offset guide lumens 184 formed in the tube walls for passage of control wires, as best shown in FIG. 6. In this embodiment, the integrally formed proximal section 140 may form a joint section (not shown) for connection to the steering section.

As was described above, the distal end of the proximal section 40 is connected to the proximal end of the steering section 44 at the distal region of the device 24, as best shown in FIG. 1. The steering section 44, in use, allows the distal tip 48 to be selectively steered, manipulated, or bent in one or more planes by action occurring at the proximal end of the device 24. Referring now to FIG. 4, there is shown one exemplary embodiment of the steering section 44. As best shown in FIG. 4, the steering section 44 includes an articulated joint 92 covered by an elastic sheath 96. In one embodiment, the articulated joint 92 includes an articulated series of ring shaped joint segments 100A-100E, although other numbers of joint segments may be used. Adjacent joint segments are connected with each other by pins 104 so that each of the adjacent ring joint segments can rotate about the pins 104. In the embodiment shown, all of the pins 104 are parallel to one another so as to lie in a common plane. As such, the steering section 44 is capable of bending in a common plane, and as a result, produces 2-way articulation when manipulated by control wires, as will be described in more detail below.

Each joint segment 100 further defines a centralized passageway 110 concentrically arranged with the central passageway of the proximal section when assembled so that optics, working devices, fluid channels, or the like, may be routed to the distal tip 48 of the device. Each joint segment 100 may further defines a plurality of axially extending guide lumens 114 disposed radially offset from the longitudinal axis of the device 24. The guide lumens 114 can be formed in the walls of the joint segments 100 and are aligned with the guide lumens of the proximal section. In the embodiment shown, the joint segments 100 include first and second guide lumens 114A and 114B that are concentrically arranged with the distal cap section guide lumens 84A and 84B for the passage of control wires, as will be described below. It will be appreciated that the number of guide lumens formed in the joint segments and their orientation effects the direction of bending of the steering section 44. In the embodiment shown in FIGS. 4-6, the steering section 44 is bendable in a single plane. As such, the guide lumens 114A and 114B are arranged 180 degrees apart and approximately 90 degrees from the pivot axis 118 of the pins 104, as best shown in FIG. 5.

While the steering section 44 has been illustrated and described as a series of ring-shaped joint segments 100 hingedly connected, it will be appreciated that other steering sections that are bendable either in one or more planes may be practiced with the present invention. For several non-limiting examples of steerable sections that may be practiced with the present invention, please see co-pending U.S. application Ser. No. 10/811,781, filed Mar. 29, 2004, U.S. Pat. No. 5,846,183, U.S. application Ser. No. 10/956,007, entitled "Video Endoscope", and U.S. Pat. No. 6,699,179 B2, which are hereby incorporated by reference. Additionally, although the joint segments 100 of the articulation joint 92 shown in FIG. 4 are generally circular in shape, it will be appreciated that other shapes could be used. For example, square joint segments as well as triangular or pentagonal cross sections, etc., could also be used to form the articulation joint.

Returning to FIG. 4, the device 24 may also include a distal tip 48, which is connected to the distal end of the steering section 44. In one embodiment, the proximal end of the distal tip 48 is provided with a joint section 130 for connecting to the distal end of the steering section 44. In the embodiment shown, the joint section 130 is a recessed slot positioned at the proximal end of the distal tip 48 for connection with the steering section 44. The joint segment 130 is sized and configured for receiving the distal joint segment 100A in a seating manner, as shown best in FIG. 2. Once seated, the distal tip 48 may then be adhesively secured, welded, bonded, or otherwise connected to the distal end of the steering section 44.

As best shown in FIG. 2, the device 24 further includes a number of control wires 140 that extend longitudinally through the device 24 from the proximal end 26 of the device 24 and terminate distally of the steering section 44. The control wires 140 terminate either at the distal end of the articulation joint 92 or at the distal tip 48. In the embodiment shown, the control wires 140 terminate with enlarged heads 142 at their distal ends, which are positioned distally of the end joint segment 100A. Alternatively, the control wires 140 may be attached to the distal tip 48 via the receipt of the enlarged heads into a pair of counterbored apertures disposed within the proximal end of the distal tip 48. As an alternative to interfacing the wires to the distal tip 48 in the aforementioned techniques, the distal ends of the control wires 140 may be directly welded to the distal tip 48 or affixed thereto by any other suitable means which maintains the control wires 140 in the desired orientation. Examples of other such affixation methods include crimping or knotting the distal ends of the control wires 140 to prevent the same from sliding through the joint segment guide lumens 84. In the embodiment shown, the device 24 includes first and second control wires 140A and 140B.

As the first and second control wires 140A and 140B extend proximally, the control wires pass through the joint segment guide lumens 114A and 114B formed in the steering section 44, the cap guide lumens 84A and 84B formed in the proximal section 40, and protrude out of the proximal end 26 of the device 24. It should be noted that the guide lumens 114 and 84 are suitably sized so that the control wires 140A and 140 B may be advanced and retracted smoothly without binding. As will be described in detail below, the proximal ends of the control wires 140A and 140 B are functionally connected to the control unit, which can effect bending of the distal end 28 by selective movement of the control wires 140A and 140B.

The control wires 140A and 140B may be of the pull or tension type, and are preferably made of a non-stretching material, such as stainless steel, braided polymer fibers, or the like. The control wires 140A and 140B are preferably carried in stainless steel or plastic sleeves 146 through the proximal section 40 so as to be protected from and to not interfere with the components routed through the central passageway of the device 24. As such, the guide lumens 84A and 84B of the distal and proximal caps 56 and 60 are configured for receiving the ends of the protective sleeve 146, as best shown in FIG. 3. While not shown, it will be appreciated that the protective sleeves 146 may extend from the proximal end of the control wires 140A and 140B to the distal end of the control wires, or along any portion thereof. In one embodiment of the invention, the control wires 140A and 140B are Bowden cables and are coated with a lubricant, such as silicone, in order to reduce friction, and the protective sleeves 146 include a lubricous liner, such as HDPE.

Returning to FIG. 2, to effect bending of the distal end 28 of the device 24 to facilitate device steering, the control wires 140A and 140B may be sequentially pulled in the proximal direction, thus imparting a tensioning force thereon. Such a tensioning force on one of the control wires deflects or bends the distal end 28 of the device 24 at the steering section 44 in the direction of the tensioned control wire as known in the art. As such, selectively pulling the control wires 140A and 140B can steer the distal tip 48 as the device 24 is advanced through the passageways of the patient. The device 24 just described is only one of many steerable devices that may be practiced with the present invention. Accordingly, any suitable steerable device having at least two opposing control wires may be practiced with the present invention.

Returning now to FIG. 1, the system 20 further includes a control unit 50 functionally connected to the proximal end of the device 24. The connection between the proximal end 26 of the device 24 and the control unit 50 allows the control wires 140A and 140B to be freely advanceable and retractable relative thereto and may prohibit contaminates or debris from entering the central passageway. In one embodiment, the proximal end of the cap 56 may include a joint section (not shown) or may be connected directly to a conventional fitting for connection to the housing (not shown) of the control unit 50. Such connections are well known in the medical device art, and thus, will not be described in detail here.

In accordance with one aspect of the present invention, embodiments of the system 20 are configured for reducing the number of motors or actuators needed to effect 2-way articulation of the distal end 28 of the device 24 in at least one plane. To that end, one illustrative embodiment of the control unit 50 will now be explained in more detail. Referring to FIG. 1, the control unit 50 includes at least one actuator 160 operatively mounted therein and at least one biasing force generating device 166. The proximal end of the first control wire 140A is functionally connected to the actuator 160 so that operation of the actuator 160 allows for the linear advancement and retraction of the control wire 140A with respect to the device body 36 to effect bending thereof as described above. The proximal end of the second wire 140B is connected to the biasing force generating device 166 such that the biasing force generating device imparts a biasing force against the second control wire 140B when the second control wire is pulled in the opposite direction (i.e. distally). In one embodiment, the proximal end of the second control wire 140B may be detachably connected to the biasing force generating device is a selective manner. Accordingly, during use, the second control wire 140B may be detached or decoupled from the biasing force generating device, if desired.

While the illustrative embodiment of FIG. 1 shows the first control wire 140A being connected to the actuator 160 and the second control wire 140B being connected to the biasing force generating device 166, it will be appreciated that the first control wire 140A may be connected to the biasing force generating device 166 while the second control wire 140B is connected to the actuator 160.

In the embodiment shown in FIG. 1, the actuator is a spool 180 rotatably driven by a motor 184, such as a DC reversible stepper motor or servo motor. Alternatively, the spool 180 may be controllably driven by other controllable electrical motors or fluid motors known in the art. In other embodiments, the actuator 160 may be other powered devices, such as a hydraulically/pneumatically powered linear actuator, a motorized linear screw mechanism, motorized rack and pinion, etc. If powered, the actuators may receive appropriate control signals from an input device, such as a joystick controller, as known in the art.

Figure 10:
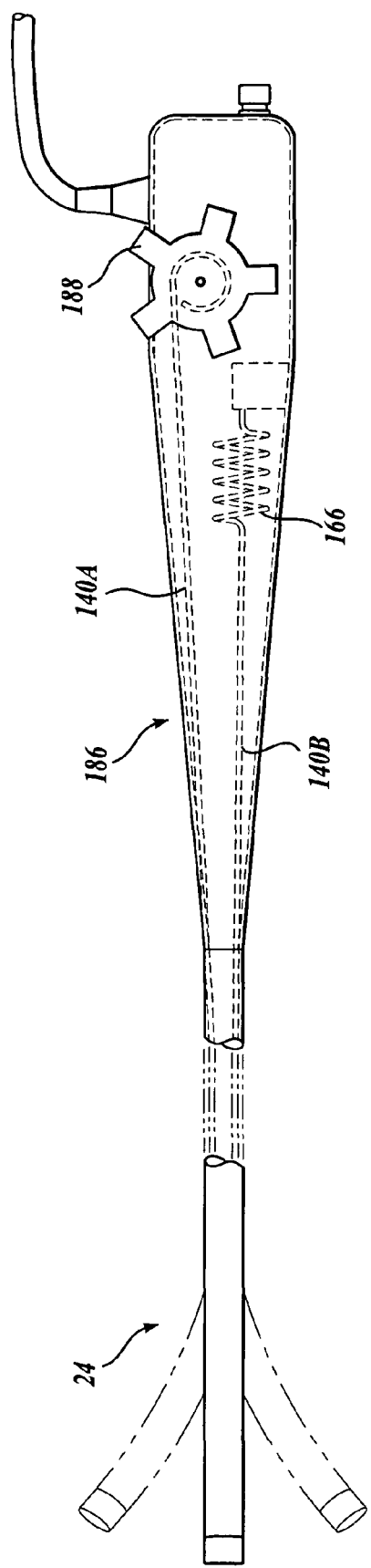
FIG. 10 illustrates an exemplary embodiment of a control unit, such as a control handle, formed in accordance with aspects of the present invention.

Alternatively, manually operated structure, such as a pivoting lever, rotating knob, etc., that are capable of advancing and retracting the first control wire 140A may be used. In one embodiment, as shown best in FIG. 8, the actuator 160 is a manual, linear slide mechanism equipped with a handle 170 graspable by the physician or assistant during use. In one embodiment, the actuator 160 may be incorporated into a manual control handle, which may also house the biasing force generating device. FIG. 10 illustrates an embodiment of a manual control handle 186 that includes a control knob 188 for effecting movement of the first wire 140A and a biasing force generating device 166 carried in the control handle 186 and connected to the second wire 140B.

As was described above, the proximal end of the second control wire 140B is connected to the biasing force generating device 166. The biasing force generating device 166 is anchored to a portion of the control unit at 190. The biasing force generating device 166 is configured to impart a biasing force against the second control wire 140B when the second control wire 140B is pulled distally, such as when the distal end 28 of the device 24 is bent in the opposite direction by proximal movement of the control wire 140A. In the embodiment shown in FIG. 1, the biasing force generating device 166 is a tension spring, e.g., a coil spring, although other devices configured by those skilled in the art for applying a biasing force against the movement of the control wire 140B in the distal direction, such as fluid or elastic dampers, leaf springs, shock absorbers, etc., may be practiced with the present invention. One such example is illustrated in FIG. 9, in which a sliding piston 194 and a compression spring 196 are utilized to generate a biasing force against the wire 140B when the control wire 140B is pulled in the opposite direction of the device 166. It will be appreciated that the spring force of the spring or other biasing force generating devices may be either variable or constant.

Figure 7A:
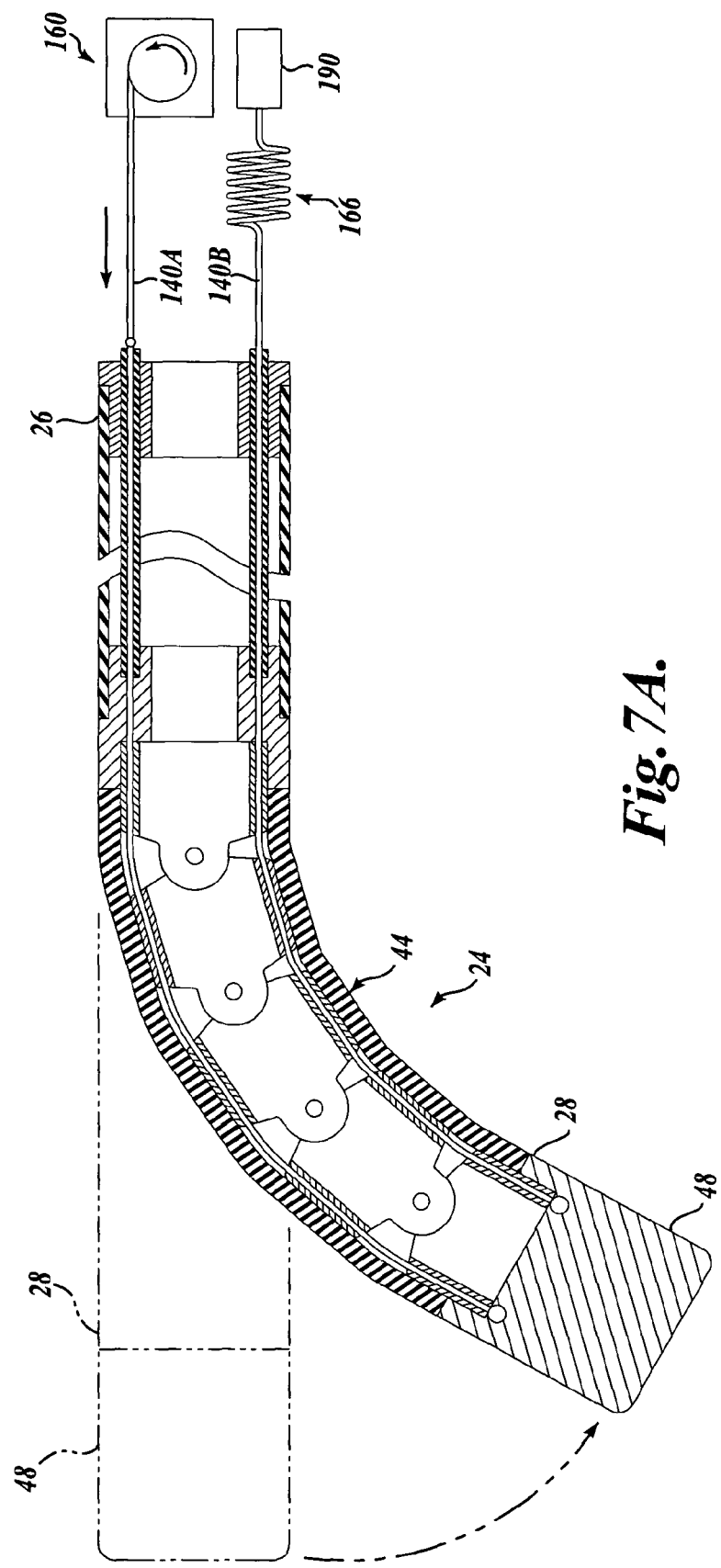
FIGS. 7A-7C are sequential views of deflecting the distal end of an endoscope by a control unit formed in accordance with one embodiment of the present invention.

The device 24, and more particularly, the control wires 140A and 140B, are connected to the control unit 50 in such a manner that allows the control unit 50 to effect 2-way articulation of the distal tip 48 in a common plane. In one embodiment, the second control wire 140B is pre-tensioned or pre-loaded prior to connection to the biasing force generating device 166 such that the distal tip 48 of the device 24 achieves a desired angle of deflection in the direction of the second control wire 140B, as best shown in FIG. 7A. To compensate for the distal tip 48 being deflected or bent to the position shown in FIG. 7A, the actuator 160 may be activated in a suitable manner to allow forward or distal movement of the first control wire 140A if connected prior to the second control wire 140B, or alternatively, the first control wire 140A may be connected to the actuator 160 after the connection of the second control wire 140B to the biasing force generating device 166.

Figure 7B:
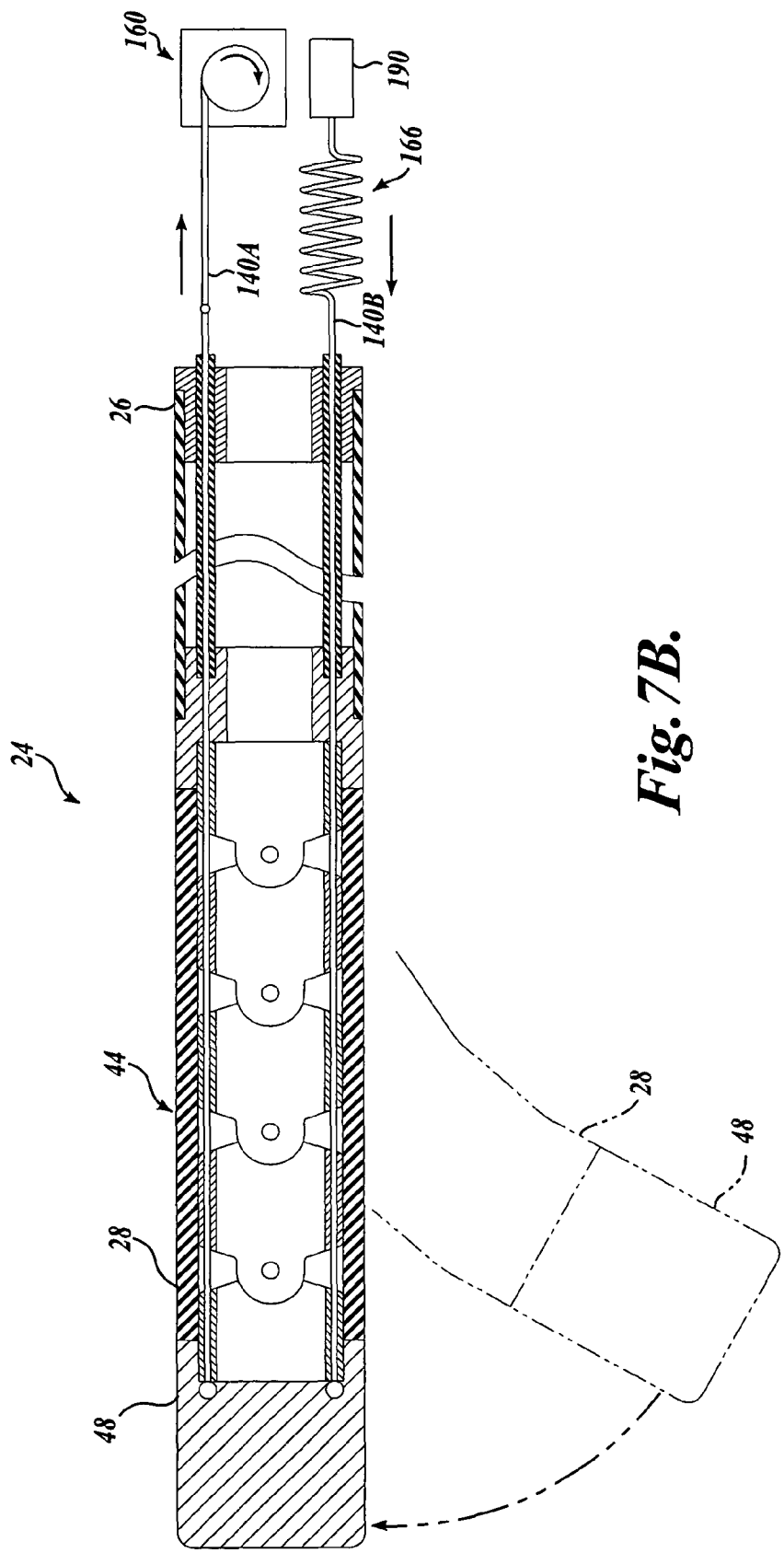

To effect bending or deflection of the distal tip 48 in the direction opposite of that shown in FIG. 7A, such as to straighten the device body 36 to the position shown in FIG. 7B, the first control wire 140A is linearly translated proximally by the actuator 160. As the first control wire 140A is pulled proximally by the actuator 160, the distal tip 48 of the device 24 deflects in the direction of the pulled control wire 140A, which in turn, causes the second control wire to be pulled distally against the biasing force generated by the biasing force generating device 166.

Figure 7C:
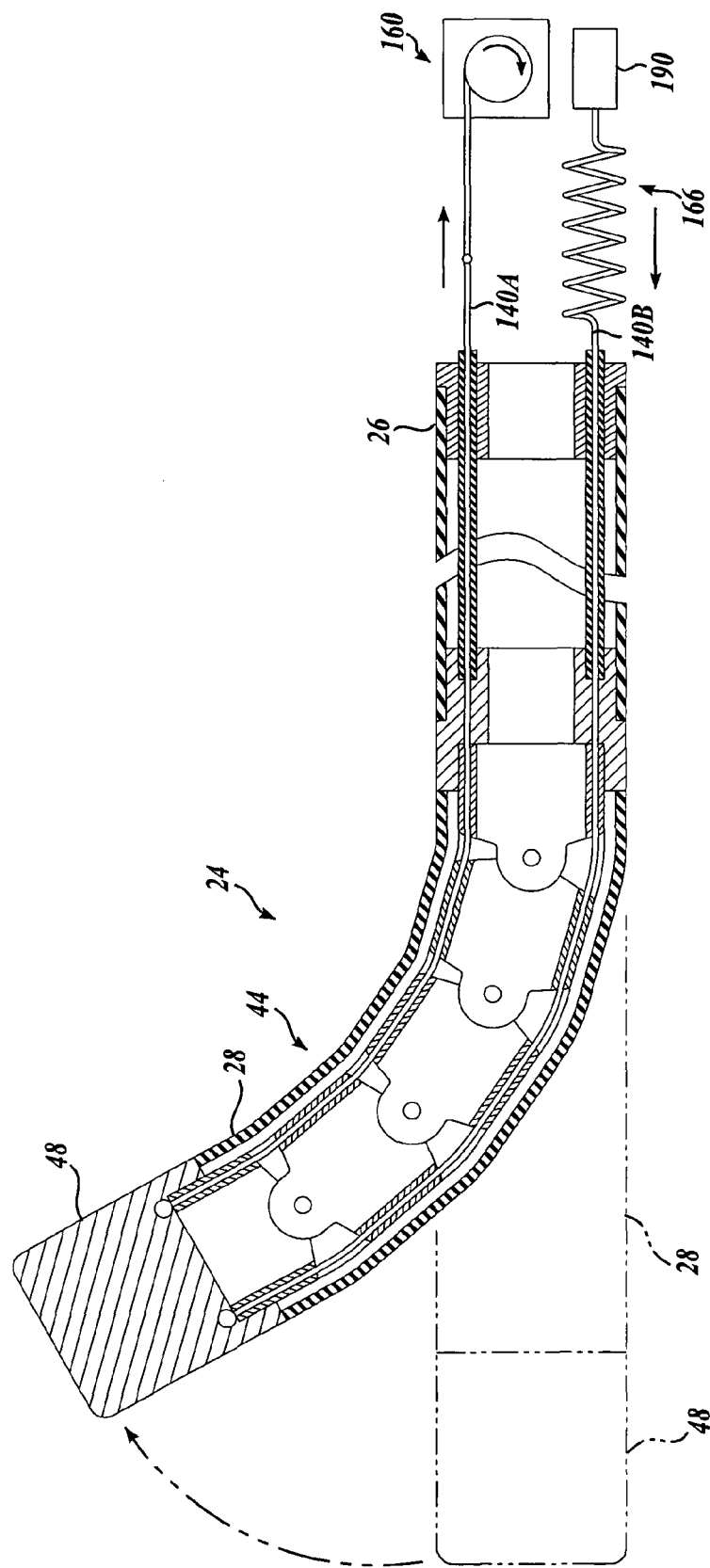

The first control wire 140A may continue to be pulled proximally by the actuator 160 against the continued biasing force of the device 166 to another deflection position, such as the one shown in FIG. 7C. It will be appreciated that the distal tip 48 may be deflected by an angle greater than the angle of deflection shown in FIG. 7A, if desired.

To return the distal tip 48 to the straightened position as shown in FIG. 7B, the actuator 160 is actuated in a suitable manner to allow the first control wire 140A to be linearly translated in the forward, i.e., distal, direction, which allows the biasing force imparted against the second control wire 140B by the biasing force generating device 166 to pull the second control wire 140B proximally so that the device 24 straightens. To return the distal tip 48 to the position shown in FIG. 7A, the actuator 160 continues to allow the first control wire 140A to be moved distally by the biasing force applied to the second control wire 140B by the biasing force generating device 166 until the distal tip 140A has achieved the position shown in FIG. 7A. Thus, the amount of initial distal tip deflection defines one deflection limit or maximum angle of deflection of the distal tip in one direction.

As was briefly described above, in one embodiment of the present invention, the device 24 may include endoscopic features for use in medical procedures that require illumination and/or visualization. To that end, a fiber optic imaging bundle and one or more illumination fibers may extend through the central passageway from the proximal end 26 to the distal end 28 of the device body 36. Alternatively, the device 24 can be configured as a video endoscope with a miniaturized video camera, such as a CCD or CMOS camera, which transmits images to a video monitor by a transmission cable or by wireless transmission. Optionally, the device may include one or two instrument channels routed through the central passageway that may also be used for insufflation or irrigation or the application of aspiration.

While the system 20 described above and illustrated herein included a steerable device having a distal end that is bendable or deflectable in one common plane, it will be appreciated that aspects of the present invention will also benefit systems that utilize steerable devices having a distal end that is bendable or deflectable in two perpendicular planes through the activation of four control wires disposed equidistant around the perimeter of the device. Several non-limiting examples of 4-way steerable devices that may be practiced with the present invention or several steering sections that my be incorporated into devices that may be practiced with the present invention are shown in U.S. application Ser. No. 10/811,781, filed Mar. 29, 2004, U.S. Pat. No. 5,846,183, and U.S. Pat. No. 6,699,179 B2, which are hereby incorporated by reference. In such systems that utilize a steerable device that is deflectable in two perpendicular planes by manipulating four control wires, the control unit 50 includes first and second actuators 160 and first and second biasing force generating devices 166 connected to the first and third and second and fourth control wires, respectively.

While embodiments of the system 20 has been described above and illustrated herein as including endoscopes or endoscopic imaging devices, steerable catheters, such as an angioplasty catheter, a catheter with sensing probes, or any other flexible or steerable device which one may wish to introduce into a place which is difficult to reach may be used. Such devices need not be confined to the medical field. Other important applications include the introduction of tools (for inspection, adjustment, or repair) in industrial applications, such as engines or other machines. For inspection purposes, fiber optics may be carried by these devices. One such device that may be practiced with embodiments of the present invention is a steerable boroscope. Thus, although the illustrative embodiments of the present invention are described primarily in terms of an endoscope or endoscopic imaging device, embodiments of the present invention have many other applications.

While the preferred embodiments of the invention have been illustrated and described, it will be appreciated that various changes can be made therein without departing from the spirit and scope of the invention. For example, it is envisioned that embodiments of the present invention may be used with an odd number of control wires, such as a three control wire system where one wire is connected to a biasing force generator and the other control wires each being connected to an actuator. It is therefore intended that the scope of the invention be determined from the following claims and equivalents thereof.

The embodiments of the invention in which an exclusive property or privilege is claimed are defined as follows:

1. A steerable medical device, comprising:
    an elongate steerable shaft having proximal and distal ends, the shaft including at least an actuatable control member and a non-actuatable control member connected at or near the distal end and extending to the proximal end thereof; and
    a control unit at the proximal end of the shaft that controls the movement of the distal end of the shaft in two directions by selectively moving the actuatable control member in proximal and distal directions, whereby movement of the non-actuatable control member is initiated by the selective movement of the actuatable control member and results from a continuous tensile force applied to the non-actuatable control member, wherein the control unit includes an actuator that is connected to a proximal end of the actuatable control member and a biasing force generator having a first end that is fixedly attached to the control unit and a second end that is connected to a proximal end of the non-actuatable control member to apply the continuous tensile force to the non-actuatable control member sufficient to bend the distal end of the shaft to a first curved position when there is no force applied to the actuatable control member by the actuator.

2. The steerable medical device of claim 1, wherein the biasing force generator is a spring.

3. The steerable medical device of claim 1, wherein the steerable device is selected from the group consisting of an endoscope and a catheter.

4. The steerable medical device of claim 1, wherein at least one of the control members includes a wire.

5. The steerable medical device of claim 1, wherein the actuatable control member is fixedly attached to the actuator.

6. The steerable medical device of claim 1, wherein the elongated steerable shaft includes a working channel having a distally located aperture.

7. The steerable medical device of claim 1, wherein the elongated steerable shaft includes an imaging device.

8. A system, comprising:
an elongate flexible shaft having proximal and distal ends and a longitudinal axis, the shaft including a steerable section and a distal tip disposed at the distal end, the shaft being bendable at the steerable section for deflecting the distal tip in at least a first and a second direction; and
at least an actuatable control member and a non-actuatable control member each having proximal and distal ends, the actuatable and non-actuatable control members routed through the shaft, the distal ends of the actuatable and non-actuatable control members being secured to the shaft at or near the distal end of the flexible shaft, whereby selective movement of the actuatable control member proximally deflects the distal tip in the first direction and selective movement of the actuatable control member distally deflects the distal tip in the second direction, whereby proximal movement of the non-actuatable control member is initiated by distal movement of the actuatable control member;
wherein the distal tip is continually biased in the first direction by a force applied to the non-actuatable control member from a spring having a first end fixedly secured within a housing and a second end connected to the non-actuatable control member, and the spring has a spring constant that is greater than that required to deflect the distal end of the shaft.

9. The system of claim 8, further comprising first and second lumens within the shaft, the first and second lumens being radially offset from the longitudinal axis of the shaft, wherein the actuatable and non-actuatable control members are routed through the first and second lumens, respectively.

10. The system of claim 8, wherein a spring rate of the spring is variable.

11. The system of claim 8, wherein the shaft is incorporated into an endoscope that includes a working channel having a distally located aperture.

12. A system, comprising:
a shaft having proximal and distal ends, the distal end being deflectable between a series of positions;
actuatable and non-actuatable control members of about equal length and having proximal and distal ends, the selective movement of the actuatable control member causing the distal end of the shaft to be deflected between the series of positions, whereby movement of the non-actuatable control member is initiated by movement of the actuatable control member; and
a control unit functionally connected to the proximal end of the shaft, the control unit including a single actuator connected to the proximal end of the actuatable control member and a single force generating device connected to the proximal end of the non-actuatable control member,
wherein the force generating device applies a continual first force on the non-actuatable control member sufficient to deflect the distal tip to a first curved position at a maximum angle of deflection of the distal end in an absence of force on the actuatable control member, and the single actuator is configured to apply a second greater force on the actuatable control member to deflect the distal tip away from the maximum angle of deflection to a second position.

13. The system of claim 12, wherein the shaft is used in a device selected from the group consisting of an endoscope and a catheter.

14. A system, comprising:
a steerable device including an elongate flexible body having proximal and distal ends, a bendable section positioned near the distal end, the bendable section being manipulatable in at least one plane and having an articulation section, and at least actuatable and non-actuatable control members each having proximal and distal ends, the actuatable and non-actuatable control members routed through the body, the distal ends of the actuatable and non-actuatable control members being secured to the body at or near the distal end of the body; and
a control unit functionally connected to the proximal end of the body, the control unit including an actuator configured to selectively move the bendable section by selective movement of the actuatable control member, wherein the actuator is connected to the proximal end of the actuatable control member, and a variable force generating device having a first end fixedly attached to the control unit and a second end connected to the proximal end of the non-actuatable control member whose nonselective movement is initiated by selective movement of the actuatable control member, the variable force generating device applying a continual first force to the non-actuatable control member sufficient to move the non-actuatable control member to bend the distal tip to a maximum curved angle of deflection in a first direction in the absence of force applied to the actuatable control member by the actuator and an increasing force to the non-actuatable control member as force is applied to the actuatable control member by the actuator to oppose straightening the distal tip in a direction opposite the first direction.

15. The system of claim 14, wherein the actuator is manually actuated.

16. The system of claim 14, wherein the actuator is motorized.

17. The system of claim 14, wherein the steerable device is selected from the group consisting of an endoscope, an imaging endoscope, a catheter, an imaging catheter, a sheath, and a shaft.

18. The system of claim 14, wherein the articulation section includes a plurality of jointed segments, each jointed segment having a first lumen configured to receive the actuatable control member and a second lumen configured to receive the non-actuatable control member, and wherein the first lumen and the second lumen are located on opposite sides of the jointed segment.

19. The system of claim 18, wherein the plurality of jointed segments are covered by an elastic sheath.

20. A control device for use with a steerable medical device having a pair of control members including an actuatable control member and a non-actuatable control member, comprising:
a housing configured for receiving the control members from the steerable medical device;
a biasing force generator carried by the housing, the biasing force generator having one end fixedly attached to the housing and a second end that is connectable to a proximal end of the non-actuatable control member; and
an actuator fixedly attached to the housing that is connectable to the actuatable control member, the actuator configured to selectively move a distal tip of the steerable medical device by selective movement of the actuatable control member, and initiate movement of the non-actuatable control member, wherein the biasing force generator is constructed to continually apply a sufficient force to the non-actuatable control member to bend the distal tip of the steerable medical device to a first curved deflection limit in a first direction and the actuator is constructed to apply a force to overcome the force applied to the non-actuatable control member by the biasing force generator and bend the distal tip in a second direction opposite the first direction away from the first curved deflection limit.

21. The steerable medical device of claim 20, wherein the biasing force generator includes a spring.

22. The steerable medical device of claim 21, wherein a spring rate of the spring is variable.

23. The steerable medical device of claim 20, wherein at least one of the control members includes a wire.

* * * * *